US011786556B2

(12) United States Patent
Gooris et al.

(10) Patent No.: US 11,786,556 B2
(45) Date of Patent: Oct. 17, 2023

(54) METHOD FOR PREPARING A GROWTH FACTORS CONTAINING PLATELET RELEASATE

(71) Applicant: Power of Platelets Pte. Ltd., Singapore (SG)

(72) Inventors: Theo Gooris, Denderhoutem (BE); Hossam Mostafa Fahmy, Cairo (EG)

(73) Assignee: Power of Platelets Pte. Ltd., Singapore (SG)

(*) Notice: Subject to any disclaimer, the term of this patent is extended or adjusted under 35 U.S.C. 154(b) by 1007 days.

(21) Appl. No.: 16/462,452

(22) PCT Filed: Nov. 20, 2017

(86) PCT No.: PCT/EP2017/079809
§ 371 (c)(1),
(2) Date: May 20, 2019

(87) PCT Pub. No.: WO2018/091713
PCT Pub. Date: May 24, 2018

(65) Prior Publication Data
US 2019/0321408 A1    Oct. 24, 2019

(30) Foreign Application Priority Data
Nov. 18, 2016  (EP) ................ 16199628

(51) Int. Cl.
| A61K 35/19 | (2015.01) |
| A61P 17/02 | (2006.01) |
| C12N 5/078 | (2010.01) |
| A61K 38/18 | (2006.01) |
| A61M 1/34  | (2006.01) |

(52) U.S. Cl.
CPC ............ *A61K 35/19* (2013.01); *A61K 38/18* (2013.01); *A61P 17/02* (2018.01); *C12N 5/0644* (2013.01); *A61M 1/3486* (2014.02); *C12N 2501/734* (2013.01); *C12N 2529/00* (2013.01)

(58) Field of Classification Search
None
See application file for complete search history.

(56) References Cited

U.S. PATENT DOCUMENTS

| 5,948,407 | A  | 9/1999  | McGuinness et al. |
| 8,535,662 | B2 | 9/2013  | Chen et al. |
| 8,734,854 | B2 | 5/2014  | Gandy et al. |
| 9,205,110 | B2 | 12/2015 | Bare |
| 2011/0008458 | A1 | 1/2011 | Gandy et al. |
| 2012/0156306 | A1* | 6/2012 | Weissman .......... A61P 7/04 514/8.1 |
| 2012/0321722 | A1* | 12/2012 | Liu .................. A61P 7/04 435/325 |
| 2013/0143810 | A1* | 6/2013 | Burnouf ............ A61K 38/1808 514/8.5 |
| 2015/0224173 | A1* | 8/2015 | Totey ................ A61K 8/983 514/8.1 |
| 2016/0051586 | A1 | 2/2016 | Delk |

FOREIGN PATENT DOCUMENTS

| CN | 103290129 A     | 9/2013 |
| CN | 203763562 U     | 8/2014 |
| CN | 104450613 A     | 3/2015 |
| EP | 0854921 A1      | 7/1998 |
| EP | 2 389 942 A1    | 11/2011 |
| EP | 2 757 879 B1    | 8/2018 |
| JP | 2011-508771 A   | 3/2011 |
| JP | 2014-501757 A   | 1/2014 |
| KR | 10-2015-0061806 A | 6/2015 |
| WO | 96/30532 A1     | 10/1996 |
| WO | 97/12040 A1     | 4/1997 |
| WO | 00/44398 A3     | 3/2001 |
| WO | 2008/034803 A1  | 3/2008 |
| WO | 2009/087560 A1  | 7/2009 |
| WO | 2012/085910 A1  | 6/2012 |
| WO | 2013/042095 A1  | 3/2013 |
| WO | 2013/113024 A1  | 8/2013 |

OTHER PUBLICATIONS

International Search Report issued in PCT/EP2017/079809; dated Apr. 24, 2018.
International Preliminary Report On Patentability and Written Opinion Bsued in PCT/EP2017/079809; dated Oct. 30, 2018.
Thierry Burnouf et al.; "Human Platelet Lysate: Replacing Fetal Bovine Serum as a Gold Standard for Human Cell Propagation?"; Biomaterials; 2016; pp. 371-387; vol. 76.
Paola Iudicone et al.; "Pathogen-free, Plasma-Poor Platelet Lysate and Expansion of Human Mesenchymal Stem Dells"; Journal of Translational Medicine; Jan. 27, 2014; pp. 1-14; vol. 12, No. 1.
Pierre-Alain Burnouf et al.; "A Novel Virally Inactivated Human Platelet Lysate Preparation Rich in TGF-β, EGF and IGF, and Depleted of PDGF and VEGF"; Biotechnology and Applied Biochemistry; Aug. 10, 2010, pp. 151-160; vol. 56, No. 4.

(Continued)

*Primary Examiner* — David W Berke-Schlessel
(74) *Attorney, Agent, or Firm* — Studebaker & Brackett PC

(57) ABSTRACT

The present invention relates to a method for preparing a growth-factors containing platelet releasate from a fluid mammalian platelet concentrate, comprising the consecutive steps of subjecting the platelet concentrate to a pathogen reduction step to disrupt non-enveloped viruses; subjecting the platelet concentrate to an activation step to cause the platelets to release growth factors; recovering a fibrinogen depleted fluid platelet releasate; subjecting the fibrinogen depleted fluid platelet releasate to a second pathogen concentration reduction step to disrupt enveloped viruses; subjecting the platelet releasate to sterile filtering and recovering a filtrate liquid containing the growth factors.
The platelet releasate obtained with the method of the present invention may be used as a therapeutic agent to enhance the proliferation of multi lineage cells in regenerative medicine and in the management of non healing wounds and resistant ulcers. The second indication is as a substitute to fetal bovine serum in in cell culture media.

27 Claims, No Drawings

(56) References Cited

OTHER PUBLICATIONS

Ian B. Copland et al.; "The Effect of Platelet Lysate Fibrinogen on the Functionality of MSCs in Immunotherapy" Biomaterials; Jul. 24, 2013; pp. 7840-7850; vol. 34, No. 32.
H. Hart et al.; "Inactivation of Viruses During Ultraviolet Light Treatment of Human Intravenous Immunoglobulin and Albumin"; Vox Sanguinis; Feb. 1, 1993; pp. 82-88; vol. 64, No. 2.
Hatim Hemeda et al.; "Evaluation of Human Platelet Lysate Versus Fetal Bovine Serum for Culture of Mesenchymal Stromal Cells"; Cytotherapy; Feb. 1, 2014; pp. 170-180; vol. 16, No. 2.
Yu-Chun Kao et al.; "Removal Process of Prion and Parvovirus From Human Platelet Lysates Used as Clinical-Grade Supplement for Ex Vivo Cell Expansion"; Cytotherapy; Jul. 2016; pp. 911-924; vol. 18, No. 7.
Michael McLaughlin et al.; "Allogeneic Platelet Releasate Preparations Derived via a Novel Rapid Thrombin Activation Process Promote Rapid Growth and Increased BMP-2 and BMP-4 Expression in Human Adipose-Derived Stem Cells"; Stem Cells International; Jan. 1, 2016; pp. 1-9; vol. 2016.
Karen Bieback; "Platelet Lysate as Replacement for Fetal Bovine Serum in Mesenchymal Stromal Cell Cultures" Transfusion Medicine and Hemotherapy; Aug. 26, 2013; pp. 326-335; vol. 40.
Lin et al., Photochemical inactivation of viruses and bacteria in platelet concentrates by use of a novel psoralen and long-wavelength ultraviolet light, Transfusion, 1997;37:423-35.
Ruane et al., Photochemical inactivation of selected viruses and bacteria in platelet concentrates using riboflavin and light, Transfusion, 2004;6:877-85.
Seltsam et al., UVC irradiation for pathogen reduction of platelet concentrates and plasma, Transfus Med Hemother., 2011;38(1):43-54.
Durante et al., Growth factor release from platelet concentrates: analytic quantification and characterization for clinical applications, Vox Sanguinis, 2011;38(1):43-54.
Mazzocca et al., Platelet-rich plasma differs according to preparation method and human variability, J Bone Joint Surg Am., 2012;94:308-316.
Lee et al., Effect of Repeated Freezing and Thawing on Biomarker Stability in Plasma and Serum Samples, Osong Public Health Res Perspect, 2015;6:357-62.
Muraglia et al., Biological activity of a standardized freezeÂ-dried platelet derivative to be used as cell culture medium supplement, Platelets, 2014;25:211-20.
Farndale, Collagen-induced platelet activation, Blood Cells Mal Dis, 2006;36(2): 162-5.

Paul et al., Molecular Mechanism of Thromboxane A2-induced Platelet Aggregation, J Biol Chem, 1999;274 (41):29108-14.
Keil et al., Treatment of Platelet Products with Riboflavin and UV Light: Effectiveness Against High Titer Bacterial Contamination, J Vis Exp, 2015; (102): 52820.
Burnouf et al., A process for solvent/detergent treatment of plasma for transfusion at blood centers that use a disposable-bag system, Transfusion, 2006;46(12):2100-8.
Mohanty, Current concepts in platelet transfusion, Asian J Transfus Sci, 2009;3(1): 18-21.
James et al., Platelet-Rich Plasma Growth Factor Concentrated Spray (Keratogrow®) as a Potential Treatment for Androgenic Alopecia, J Stem Cells, 2016; 11(4):183-189.
Sloan, The normal platelet count in man, J Clin Path, 1951;4:37.
Communication Pursuant to Article 94(3) EPC issued in EP Application No. 17 851 829.6-1112; dated Sep. 29, 2020.
Third party observation against PCT/EP2017/079809; dated Feb. 20, 2019.
Simon Buntinx, "Platelet-Rich Plasma on the Horse", Master's Thesis, 2015, Faculty of Veterinary Medicine, University of Ghent, Belgium, total 44 pages.
Sergeeva et al., "Analysis of Reparative Activity of Platelet Lysate: Effect on Cell Monolayer Recovery In Vitro and Skin Wound Healing In Vivo," Bulletin of Experimental Biology and Medicine (a translation of Kletochnye Tekhnologii v Biologii i Meditsine), 162(1), Nov. 23, 2016, pp. 138-145, doi.org/10.1007/s10517-016-3563-3.
Obata et al., "Effect of autologous platelet-rich plasma-releasate on intervertebral disc degeneration in the rabbit anular puncture model: a preclinical study," Arthritis Research & Therapy, 14(6):R241, Nov. 5, 2012, pp. 1-11, doi: 10.1186/ar4084.
Sampaio-Barros et al., "Undifferentiated spondyloarthritis: a longterm followup," The Journal of Rheumatology, 37(6), May 1, 2010, pp. 1195-1199, doi: 10.3899/jrheum.090625.
Plöderl et al., "Development and validation of a production process of platelet lysate for autologous use," Platelets, 2011; 22(3), published online: Dec. 15, 2010, pp. 204-209, doi: 10.3109/09537104.2010.531304.
Wolfe, "Determinants of WOMAC function, pain and stiffness scores: evidence for the role of low back pain, symptom counts, fatigue and depression in osteoarthritis, rheumatoid arthritis and fibromyalgia," Rheumatology, 38(4), Apr. 1999, pp. 355-361, doi: 10.1093/rheumatology/38.4.355.
Guan et al., "Big data modeling to predict platelet usage and minimize wastage in a tertiary care system", Proc Natl Acad Sci U.S.A., 114(43), pp. 11368-11373, Oct. 2017, doi: 10.1073/pnas.1714097114.

* cited by examiner

METHOD FOR PREPARING A GROWTH FACTORS CONTAINING PLATELET RELEASATE

The present invention relates to a method for preparing a growth-factors containing platelet releasate from a mammalian platelet concentrate, according to the preamble of the first claim.

Mammalian platelets contain a myriad of bioactive agents with important physiological functions. Amongst those, growth factors are of particular interest because of their role in the enhancement of different cell line proliferation and tissue regeneration, both of which are of significant importance in regenerative medicine, wound and ulcer healing.

The concept of using a patient's own platelet rich plasma (PRP) in dentistry, plastic surgery and regenerative medicine already developed in the early 1990s. Platelets were obtained either by centrifugation of the patient's own anticoagulated whole blood, or by using special devices such as Medtronic's Magellan or Harvest's SmartPrep. This use of autologous platelets could however be jeopardized with anaemic patients or in case of the need to use large quantities or over long periods of time. One of the most important limitations of autologous PRP is the need to a dedicated machine or laboratory for preparing the platelets concentrates. To make them suitable for use, the platelets namely are activated to cause them to release the content of their alpha granules. However, it is indispensable to use the PRP within a few hours after its separation from the patient, as otherwise the growth factors contained therein risk to loose a substantial portion of their bioactivity.

Several techniques have been described for preserving platelets. Addition of DMSO and trehalose are two examples of suitable methods for prolonging preservation of platelets, both for platelets that have been subjected to lyophilization (freeze-drying) or not. Cryoprotectant compositions used along with lyophilization processes led to a similar result in relation to preservation. Disadvantages of these approaches which merely use preservatives and/or lyophilization on intact platelets, relate to the fact that proteins, receptors and the like are retained on the platelet surface or within the platelets. For example, several platelet membrane receptors remain intact for binding with extracellular factors in response to platelet activation, e.g., for platelet adhesion, aggregation, etc.

It would therefore be beneficial to dispose of a more universal method which would permit to convert blood platelets into a preparation which is suitable for effective use in a wide variety of applications, including wound healing, skin treatment, treatment of disorders of body tissue (including body organs) such as lung tissue, and the like. Thereby, likely, the risk to unwanted interaction of such a preparation with extracellular factors should be minimal.

WO2013113024 discloses a method of preparing a composition suitable for therapeutic use or for use as a culture medium, wherein platelets are concentrated and subjected to lysing to disrupt the platelets' membrane. At least 30% of the platelets can be lysed. The lyophilized platelet lysates are formed in a composition which also contains released concentrations of available growth factors, cytokines, and chemokines. WO2013113024 also discloses a method of treating mammalian tissue, which comprises the steps of applying to a mammalian tissue site for treatment, the above-described composition including lyophilized platelet lysates. In one example, the lyophilized platelet lysates are prepared from source platelets, wherein at least 30% of the source platelets are lysed to form the lyophilized platelet lysates. However, the lysate are not depleted of fibrinogen and WO2013113024 does not recognise the problem of viral or pathogen infection and does not solve that problem.

EP2389942 discloses a method for preparing a virally-inactivated growth factors-containing platelet lysate depleted of platelet derived growth factors (PDGF) and vascular endothelial growth factors (VEGF), which is suitable for in vitro or ex vivo cell culture and for promoting the proliferation and/or the differentiation of stem cells towards osteoblast lineage and/or chondrocytes. The method comprises the steps of contacting and incubating a platelet concentrate with 0.2 to 5 vol. % of a solvent and/or a detergent for a period of 5 minutes to 6 hours, at a pH from about 6.0 to about 9.0, and at a temperature between 2° C. and 50° C., removing the solvent and/or the detergent by oil extraction to obtain an aqueous protein phase, and incubating the aqueous protein phase with charcoal to remove the solvent/detergent. A preliminary step may comprise preparing a starting platelet concentrate, by apheresis or by buffy-coat isolation from whole blood, which may either be fresh, expired and stored liquid or expired and stored frozen. In a preferred embodiment, the platelet lysate comprises the growth factors TGF-β, IGF, EGF and/or bFGF. The method disclosed in EP2389942 however presents several disadvantages. Although the platelet lysate could be suitable for in vitro or ex vivo cell cultures, it is expected to be insufficiently effective for clinical application in regenerative medicine purposes including bone fracture healing, since the complete cocktail of all platelet derived factors, in particular PDGF and VEGF is needed for clinical use of platelets lysates in regenerative medicine, as in wound healing. The solvent extraction gives a low platelet yield, often of 10-15 vol. % with respect to the original volume only. EP2389942 does not include a fibrinogen depletion step, an does not include a lyophilisation step. The solvent/detergent viral inactivation applies only to enveloped viruses but is not capable of inactivating non-enveloped viruses such as the Hepatitis A virus and the Parovirus B19, nor does the solvent/detergent treatment remove other potential contaminants such as bacteria or other microorganisms U.S. Pat. No. 8,734,854 discloses a method for releasing growth factors from a patient's whole blood or plasma in a non-destructive medium. The growth factors obtained from that method are suitable for topical application to a surface wound area to promote wound healing, for injection into soft tissue such as a torn tendon to promote tissue growth and healing. In another method the growth factors are released from a whole blood source and freeze dried by conventional lyophilization. The freeze dried product may be reconstituted by normal saline for treatment of a patient's wound or for use in a surgical procedure. Although U.S. Pat. No. 8,734,854 discloses that the final product may be lyophilized, lyophilisation alone proved to be insufficient to provide reliable removal of pathogens. Moreover, the growth factors obtained from the method of U.S. Pat. No. 8,734,854 is not fibrinogen depleted.

Other known platelet released growth factors include those developed by Cambium Medical Technologies Allogeneic Pooled Human Platelet Lysate. The product is not yet present as a commercial product and although it is said to be fibrinogen depleted, there is no indication that it has been subjected to pathogen/viral reduction treatment.

Numerous articles discuss the role of platelet released growth factors as a substitute of fetal bovine serum. A review is given in Platelet Lysate as Replacement for Fetal Bovine Serum in Mesenchymal Stromal Cell Cultures, Transfus Med Hemother 2013; 40:326-335.

EP2757879 discloses a method for preparing a platelet lysate, capable of acting as a co-adjuvant for the isolation and/or growth and/or expansion of stem cells, fibroblasts or dendritic cells. The method comprises the steps of (a) isolating a buffy coat fraction from a mixture of whole blood samples obtained from at least two subjects; (b) exposing the isolated buffy coat fraction to a photochemical agent and to UV radiation to remove any contaminating agents present; (c) subjecting the buffy coat fraction to at least one freezing/thawing cycle to achieve lysis of the platelets contained therein; (d) centrifuging the fraction and collecting the liquid phase. The platelet lysate thus obtained can be used as a co-adjuvant for the culture, growth and/or expansion of stem cells, in particular mesenchymal, of mesenchymal stem cells derived from adipose tissue, fibroblasts and dendritic cells. The platelet lysate obtained with the method disclosed in EP2757879 is however not fibrinogen depleted, it is doubtful whether freezing/thawing cycles are capable of causing an efficient release of growth factors and whether or not the activity of the growth factors is affected by the repeated freeze/thaw cycles, and the method only uses one single pathogen removal step.

Commercial platelet lysates are available, for example those from Macopharma. Unfortunately, these lysates are made available as large frozen volumes, which need to be downscaled to smaller size aliquots after thawing, with potential risk of microbiological contamination. The human Platelet Lysate by Millipore, PLTMax, and those provided by Zenbio also are available only in large frozen volumes; they are meant for research purposes only and are not intended for ex vivo therapeutic use.

According to T. Burnouf et al., Biomaterials 76 (2016), 371-387 growth factors and cytokines stored in platelet granules can be released by direct activation using addition of a calcium chloride salt solution, by fibrin formation and platelet degranulation, or using thrombin. Other techniques for inducing release of growth factors and other biomolecules from platelets include repeated freeze/thaw cycles, sonication alone or in combination with freeze/thaw cycles, or a solvent/detergent treatment which also inactivates lipid-enveloped viruses. However, subjecting of the platelets to repeated freeze/thaw cycles is thought to impact the growth factors. The risk to transmission of infectious agents is managed by mandatory testing of each individual donation and not using confirmative donations. Mandatory testing is advised for detection of HIV-1/HIV-2, antibodies, hepatitis B surface antigen, hepatitis C virus antibodies.

There is thus still a need to a method for the preparation of platelet derived growth factors which provides an optimal yield of the growth factors, and which shows a minimal risk to the presence of pathogens, including lipid enveloped as well as non-enveloped viruses and bacteria.

It is therefore the object of the present invention to provide a method for the preparation of platelet derived growth factors from a mammalian platelet concentrate which permits achieving an optimum yield of the growth factors, which shows a minimal risk to the presence of enveloped as well as non-enveloped viruses, bacteria, fungi, and other blood borne micro-organisms.

In a preferred embodiment it is an object of this invention to provide a method for the preparation of platelet derived growth factors with an improved pathogen inactivation not only of the most common pathogens, but also of pathogens that cannot or can hardly be inactivated with the existing techniques.

Another preferred embodiment of this invention aims at providing a platelet releasate which is suitable for use in regenerative medicine and wound management. A further preferred embodiment aims at providing a platelet releasate which may be used as a substitute to fetal bovine serum in cell culture media.

The problem of providing a method for the preparation of platelet derived growth factors from a mammalian platelet concentrate which provides an optimal yield of growth factors, wherein the platelet derived growth factors show a minimal risk to the presence of pathogens, including lipid enveloped as well as non-enveloped viruses, bacteria, and other blood borne pathogens outlined above may be solved according to the present invention with a method which shows the technical features of the characterising portion of the first claim.

Thereto, the method for preparing a growth-factors containing platelet lysate of this invention comprises the consecutive steps of a. subjecting the platelet concentrate to a first pathogen concentration reduction step with the purpose of disrupting both DNA and RNA of micro-organisms present in the platelet concentrate, wherein micro-organisms include enveloped, non enveloped virus, or bacteria, fungi, etc;

b. subjecting the platelet concentrate to an activation step by contacting it with an activating agent to cause the platelets to release at least part of alpha granules and growth factors present therein, thereby providing a fluid platelets releasate;

c. subjecting the fluid platelet releasate to a fibrinogen concentration reduction step and recovering a fibrinogen depleted fluid platelet releasate; this step aims at reducing the concentration of fibrinogen in the fluid platelet releasate;

d. subjecting the fibrinogen depleted fluid platelet releasate to a second confirmatory pathogen concentration reduction step with the purpose of disrupting enveloped viruses;

e. subjecting the platelet releasate to sterile filtering and recovering a filtrate liquid containing the growth factors.

The method for preparing a growth-factors containing platelet lysate of this invention comprises the consecutive steps of (a) subjecting the platelet concentrate to a first pathogen concentration reduction step. In a preferred embodiment, the first pathogen concentration reduction step comprises a step of incubating the platelet concentrate with a photochemical active agent and exposing the platelet concentrate to UV irradiation. This step permits obtaining a platelet concentrate with a reduced pathogen content, due to the inactivation or disruption of the RNA and/or DNA of the micro-organisms present in the platelet concentrate. In particular a platelet concentrate results in which the concentration of enveloped and non-enveloped viruses is reduced. This first step may also permit to inactivate other blood borne micro-organisms contained in the platelet concentrate;

(b) subjecting the thus treated platelet concentrate to an activation step by contacting the platelet concentrate with an activating agent to cause the platelets to release at least part of their content, in particular at least part of the alpha granules present in the platelets as well as the content of these alpha granules including the growth factors, and to provide a platelet releasate. The platelet releasate will usually take the form of a fluid composition, which contains what remains of the activated platelets and the content of the platelets that has been released in the activation step. As a result of this activation step, supra physiological doses of growth factors and cytokines will be released from the platelets into the composition or solution comprising the platelet concentrate, in addition to fibrinogen. This is important as the alpha granules usually contain the majority of the growth factors. Activation of mammalian platelets and their concentrates may be achieved by contacting them with a platelet activator capable of inducing platelet rupture and of causing at least part of the content to be released, including supra-physiological doses of growth factors, cytokines and chemokines. Suitable activators include aqueous solutions of calcium salts for example calciumchloride, thrombin, collagen, thromboxane A2 and adenosine diphosphate (ADP). Addition of thrombin causes a huge clot to be formed, which contains virtually the whole content of the platelet concentrate. Incubation at a temperature around body temperature, about 37° C. for a time which is sufficiently long, often 3 hours or more, causes the clot to shrink to a negligible size, with expression of all growth factors within entrapped platelets. The present invention therefore may achieve that a volume of growth factors suspended in plasma is released which is almost identical to the initial volume of platelets concentrate.

(c) Subjecting the fluid platelet releasate to a fibrinogen reduction step and recovering a fluid, fibrinogen depleted releasate. This step in fact contains the steps of isolating the fibrin clot formed following the interaction of the fibrinogen released from the platelets with the activating agent added in the previous step to cause release of the content of the platelets. It is adviseable to remove the fibrinogen that is released upon activation of the platelets as much as possible from the releasate, since it may give rise to the formation of a semisolid gel which could cause a nuisance when blood plasma that has been enriched with platelets (PRP), is further used for example as an intra lesion injection in injuries of the musculoskeletal system including tendons, ligaments and joints, or in facial rejuvenation or in any other treatment. Nevertheless, the fibrinogen concentration of blood platelets is lower than that of plasma. The method of this invention may further contain the step of isolating fibrinogen from the platelet releasate and recovering for further use the fibrinogen depleted platelet releasate;

(d) subjecting the fibrinogen depleted platelet releasate to a second pathogen concentration reduction step to disrupt or inactivate enveloped viruses, and recovering an aqueous protein phase containing the growth factors. The primary goal of this step is to confirm the removal of enveloped viruses such as lipid enveloped HBC, HCV and HIV enveloped viruses. The use of two orthogonal pathogen inactivation steps (step a and step d) as is done in the present invention is particularly important, as it permits to achieve inactivation of both non-enveloped and enveloped viruses, as well as inactivation of larger microorganisms such as bacteria and parasites such as protozoae. The method of this invention therewith responds to an essential requirement of modern regulations of the blood derived products of the biopharmaceutical industry. This step ensures that the risk to unwanted interaction with extracellular factors may be minimized.

(e) subjecting the fibrinogen depleted platelet releasate to sterile filtering with the purpose of removing any remaining solid material and bacteria and recovering the growth factors containing liquid or fluid filtrate. As the platelets originate from mammalian blood, the liquid or fluid filtrate will mainly be water based or be an aqueous solution which comprise a protein phase.

In the above-described method, the steps are preferably carried out consecutively in the described order In addition to the first step a which permits to achieve inactivation of non-enveloped viruses present in the platelet concentrate, the method of this invention also contains a step for inactivating enveloped viruses, generally lipid enveloped viruses, which may be contained either in the platelet concentrate or in the platelets as such. A preferred method for achieving this is subjecting of the platelet releasate to or contacting it with a solvent and/or detergent with the purpose of dissolving lipid membranes contained in the releasate and destructing the nucleic acids contained therein, followed by an extraction step preferably with oil to remove the solvent and/or detergent containing the dissolved lipid membranes, and a filtration step to remove any remaining solids. Because of the presence of an extraction and filtration step, lipid-enveloped viruses as well as other pathogens like bacteria and parasites such as protozoae may be inactivated and plasma and platelet lipids which may be contained in the initial platelets concentrate may be removed. The process steps of oil extraction and filtration permit an easy, rapid and efficient preparation of a virally and bacterial inactivated growth factors containing platelet releasate, wherein solvent and detergent concentrations are meeting the limits approved by regulatory authorities for parenteral blood-derived therapeutic products.

The present invention us provides a method for preparing a growth-factors containing platelet releasate, with which the risk to transmission of residual bloodborne diseases by an incalculable factor, especially in the case of platelet products which originate from a blood product that has systematically been subjected to leukocyte removal, may be minimised. Leukocyte removal namely has the effect that the self-sterilization capacity of blood is lost to a large extent, and often is completely lost. This is important as plasma constitutes an optimal medium for survival or growth for a wide variety of pathogens.

Moreover, because of the selected combination of pathogen inactivation treatments absolute safety of the platelet derived growth factors obtained with the present invention may be ensured. Mixtures of virally-inactivated platelet-derived growth factors may therefore be provided, which can be efficiently standardized for use in therapeutic treatments, cell therapy or cell culture. The double step of viral/pathogen inactivation qualify the product obtained by the process of this invention to be safely used in clinical research and mesenchymal stem cell expansion for in vivo application. As a result, the need to the use of autologous platelets with a patient, with the associated limitations is obviated. Additionally, in stead of imposing the use of autologous platelets, the present invention opens the possibility of using platelet releasate obtained from a pool of mammalian blood products, which originate from several subjects, at minimal risk to transmission of bloodborne diseases, which may originate from one or more of the subjects from which the platelet concentrate originates.

The method of this invention is not only suitable for preparing human platelet derived growth factors, but may also be used with minimal adjustments to produce equine derived growth factors from animal platelets, for example from horse platelets with similar medical applications. Reconstituted lyophilized platelet derived growth factors may further be used as an alternative of fetal bovine serum in cell culture media and in mesenchymal stem cell expansion.

Considering the fact that, in part due to the risk of bacterial contamination and loss of functional activity for hemostasis, platelets usually have a limited shelf life of 5 or 7 days, when clinically used intravenously for the correction of quantitative or functional thrombocytopenia, a high number of platelet units older than 5 or 7 days are usually discarded each year. In allowing expired platelets stocks to be used for the preparation of platelet-derived products such as the platelet releasate of this invention, the method of the invention reveals a promising economical interest.

This invention further permits maximising the amount of releasate volume obtained, by carrying out the process steps in the sequence described above. Modern techniques such as the Mirasol™ system, permit to subject large amounts of platelets concentrates collected by platelets pheresis to pathogen inactivation, at minimal risk to reducing the collected platelet volume. By carrying out the oil extraction step only after a first viral inactivation has been carried out, loss or reduction of the amount of releasate available as a consequence of the pathogen removal treatments, may be reduced to a minimum.

Since the use of freeze/thaw cycles may be avoided, the present invention presents the additional advantage that there is a minimal risk that the content in the major proteins of the growth factors obtained therewith, such as albumin and immunoglobulins, as well as the concentration of growth factors in the releasate other than platelet derived growth factors (PDGF) and vascular endothelial growth factors (VEGF), such as TGF-β1, EGF, and IGF, would be adversely affected.

In a preferred embodiment, the growth-factors containing platelet releasate obtained with the method of this invention may be lyophilized in small volume vials that could be easily reconstituted in a single step by addition of water or a saline solution, according to actual needs. Thereby the volume is preferably selected such that it contains a number of growth factors which is sufficient for one treatment. Intra and inter batch concentration of growth factors per vial may be standardized by adjusting the volume of released growth factors dispensed in each vial according to the initial platelet count, i.e. the amount of platelets that is subjected to the consecutive steps (a) through (e) described above. In a preferred embodiment, the liquid filtrate obtained in step (e) above is divided in individual volumes, wherein each individual volume is adjusted such that it originates from between $2 \times 10^5$ and $2 \times 10^7$ platelets per $cm^3$, preferably about $2 \times 10^6$ platelets per $cm^3$. If so desired, the platelet releasate may be enriched for a certain set of growth factors, depending on the intended use. By standardising the number of growth factors for each vial, the need of making smaller aliquots out of a larger stock volume with potential risks of contamination and loss of activity because of repeated thawing and freezing cycles to which the stock must be subjected to permit extraction of a desired small aliquot, may be obviated.

In the above, the wording "platelet concentrate" refers to any fluid, either biological or artificial, which contains platelets. Non-limiting examples of such fluids include various forms of whole blood, blood plasma, platelet rich plasma, concentrated platelets in any medium, or the like, derived from mammalian sources, which may be human or animal. The fluid will generally be water based. Thereby the fluid may be autologous or it may be a pool of allogenic fluids which originate from several different subjects, for example from apheresis or buffy coat derived platelet concentrates with a certain minimum platelet content, routinely prepared at blood banks. Usually manufacturing will be standardized of allogeneic off-the-shelve products. Platelet concentrates will generally be prepared using the buffy coat method which employs whole blood, the PRP method, or apheresis platelets, which originate from stored individually donated blood portions. The use of the latter is preferred, in particular when additionally subjected to pre-storage leukocyte depletion. Furthermore, platelet concentrates that cannot be transfused because they have reached the five to seven day storage limit, can be frozen, stored and used as growth medium supplement.

The platelet concentrate can be maintained in plasma or in a mixture of plasma and an additive solution. In order to increase shelf life, platelet concentrates may consist of large pools of frozen platelet concentrates.

The term "concentrate" or "concentrating" may refer to the separation of platelets from the bulk of the plasma, whole blood, or other fluid from which it is present, but it may also refer to the original product as such for example to whole blood or plasma. Centrifugation, spectrometry, filtration, decanting, gravity settling, or other methods of concentrating platelets from platelet-containing fluids can be used for producing a concentrate. When concentrating platelets, it can be desirable to use an anticoagulant (particularly for centrifugation or gravity settling) along with the source of platelets to prevent clotting during the separation of platelets from other components of the blood, plasma, or other fluid. The term "anticoagulant" refers to compositions that inhibit clotting when concentrating or collecting platelets for use in accordance with examples of the present disclosure. Anticoagulants generally are available as inhibitors of clotting factor synthesis, inhibitors of thrombin, or antiplatelet drugs. Inhibitors of clotting factor synthesis that inhibit the production of certain clotting factors in the liver, include compositions such as warfarin (Coumadin). Inhibitors of thrombin interfere with blood clotting by blocking the activity of thrombin, and include compositions such as heparin and lepirudin (Refludan). Antiplatelet drugs interact with platelets themselves, and include drugs such as aspirin, ticlopidine (Ticlid), clopidogrel (Plavix), tirofiban (Aggrastat), eptifibatide (Integrilin), etc.

In the above, the term "platelet releasate" refers to the composition obtained when a platelet concentrate is subjected to an activation step and the content released by the platelets is recovered as has been described above, in particular step b as described above.

In the above "subjecting the platelet concentrate to an activation step or an activation treatment" means destroying the platelets by disrupting their cell membrane to achieve that the platelets release their granule content, in particular the alpha granules contained in the platelets. Activated platelets may release a wide variety of compounds contained therein, a.o. proteins, cellular micro vesicles for example plasma membrane derived micro particles, exosomes, growth factors such as VEGF, bFGF, PDGF, TGF-β and other cytokines. This can be done chemically, mechanically, by fluid homogenization, or sonication, or by lyses. But according to this invention, activation is preferably carried out by contacting the platelet concentrate with an activating agent as this permits to maximise release of the platelets content into the fluid platelet releasate. Suitable lysing agents include thrombine, collagen, thromboxane A2 or ADP and calcium salt solutions or a mixture of two or more hereof. An example of a suitable calcium salt is calcium chloride. However any other lysing agents considered suitable by the skilled person may be used as well.

Mechanical lysing may for example be carried out using a freeze-thaw cycle, by freezing a platelet suspension and then thawing the material to above room temperature, e.g., 30° C. to 45° C. This method causes cells to swell and break as ice crystals form, followed by contraction at thawing. The cyclical swelling and contracting ultimately causes the platelets to break open. Depending on the number of freeze thaw cycles, varying degrees of platelet cytolysis may be achieved, e.g., at least 30%, at least 50%, at least 70%, at least 90%, or up to 100% cytolosys, by platelet count. Within the present invention mechanical lysing may be considered, but is preferably dispensed with because of the suspected quality loss of the releasate.

Within the scope of this invention "lyophilized platelet releasates" includes "lyophilized platelet rich plasma releasates" or "LPRRL" as a specific type of lyophilized platelet releasates without however being limited thereto.

Within the scope of this invention "anticoagulant" is a composition that inhibits clotting when concentrating or collecting platelets for use in accordance with the present invention. Anticoagulants generally are available as calcium ions complexing/chelating agents, inhibitors of clotting factor synthesis, inhibitors of thrombin, or antiplatelet drugs. Inhibitors of clotting factor synthesis that inhibit the production of certain clotting factors in the liver, include compositions such as warfarin (Coumadin). Inhibitors of thrombin include compositions such as heparin and lepirudin (Refludan). Antiplatelet drugs interact with platelets themselves, and include drugs such as aspirin, ticlopidine (Ticlid), clopidogrel (Plavix), tirofiban (Aggrastat), eptifibatide (Integrilin), etc.

The UV irradiation carried out in step a of the method of this invention preferably involves exposing the platelet releasate to UVA irradiation, preferably an exposure to UVA radiation of an energy density of between 1 and 10 $J/cm^2$, more preferably about 3 $J/cm^2$. Exposure to UV irradiation is preferably carried out after the platelet releasate has been incubated with a photochemical agent, in particular a psoralen, in particular amotosalen, or riboflavin.

In step d of the method of this invention where the platelet releasate is contacted with a solvent and/or detergent to dissolve the membrane of enveloped viruses or other pathogens, preferably use is made of a solvent for incubating the platelet concentrate selected from the group of di- or trialkylphosphates, and is preferably tri-n-butylphosphate. Suitable detergents for use in step d of the method of this invention include detergents selected from the group of polyoxyethylene derivatives of fatty acids, partial esters of sorbitol anhydrides, non-ionic detergents, sodium deoxycholate and sulfobetaines, and is preferably Triton X-45, Triton X-100 or Tween 80.

The amount of oil used in the subsequent extraction step for removing the solvent and/or detergent and the components dissolved therein, may be varied within a wide range, but preferably the amount of oil ranges from 2 to 20 weight %, preferably from 5 to 15 weight %, more preferably from 5 to 10 weight %, based on the total volume of the mixture of the platelet concentrate and the solvent and/or the detergent. Thereby, preferably use is made of a pharmaceutical grade oil, for example castor oil. In an extraction process typically a certain volume of oil is added to the platelet releasate, and subjected to shaking on a blood mixer for a certain period of time, typically 30, 20 or 15 minutes or less. Thereafter the container in which the extraction is carried out may be suspended in an inverted position for a certain period of time, for example 10 minutes or less or longer, to obtain an upper oil phase and a lower platelet releasate phase, which is separated by gravity from the upper phase. This step may be repeated once or twice or more times, depending on the extraction efficiency.

The method of the present invention may include after the extraction step e, at least one step of centrifugation to separate the platelets from the oil and an aqueous protein phase. Usually the platelet releasate is subjected to centrifugation at low temperature, typically below 10° C., preferably below 5° C., typically about 4° C., preferably in an inverted position to separate any remanants of oil in an upper phase and the platelet releasate in a lower phase that is obtained by gravity.

The method of the present invention may include after the filtering step e, a lyophilisation step, to prolong the shelf life of the platelet releasate. Before being subjected to lyophilisation the liquid or fluid filtrate obtained in step e may be divided in several volumes, the volume being adjusted such that each volume contains the releasate of a predetermined amount of platelets per $cm^3$, for example the releasate of about $2\times10^5$ to $2\times10^7$ platelets, more preferably the releasate of about $2\times10^6$ platelets per $cm^3$, but any other concentration of platelets may be selected by the skilled person. The product obtained with the method of this invention combines the characteristics of being lyophilized in reasonable volumes which are suitable for immediate use without requiring further division into suitable aliqouts, with ease of storage and reconstitution, and being fibrinogen depleted.

In a preferred embodiment, in order to achieve cryoprotection of the growth factors, in advance of lyophilisation, human albumin is supplied to the liquid filtrate obtained in step e.

Within the scope of this invention "lyophilization," refers to a freeze-drying or dehydration process that is often used to preserve platelets. Lyophilization may however also be used not just as a preservative process, but rather also as a treatment for lysing platelets, to further lyse platelets after initial freeze-thaw or other lysis technique is conducted. In other words, in accordance with examples of the present disclosure, after releasates are formed as described herein, lyophilization provides the added benefit of preserving the growth factors, cytokines, chemokines, and other contents initially enclosed within or bound to the surface the platelets, but which are released when platelets are lysed as described herein, e.g., freeze-thaw lysing. The process is typically carried out by freezing the material and reducing surrounding pressure to allow frozen water in the material to sublimate directly from the solid phase to the gas phase.

If so desired, the platelet concentrate may be subjected to a leukocyte removal step in advance of subjecting the platelets to an activation step to cause their content to be released. Leukocyte removal mainly aims at reducing the risk to the occurrence of unwanted complications associated with transfused white blood cells present in units of red blood cells and platelets.

The method of the present invention is intended for the preparation of fibrinogen depleted blood platelet releasate rich in growth factors from mammalian platelet concentrate which could be human or animal platelets, for example horse platelets. The releasate may be lyophilised or not.

Platelet releasates obtained with the method of this invention can be used to treat wounds, ulcers, or burns. The platelet releasates can be applied in dry form or rehydrated form prior to application, or as a gel. Alternatively, even if the skin is not damaged by a wound, ulcer, or burn, it can be used for repairing other types of damage that occurs as a result of aging, photodamage, pathological or degenerative disease, or the like. The concentration of the platelets in the platelet releasates obtained with the method of this invention can vary within wide ranges, but preferably the concentration is as high as possible to achieve a maximum effect.

In the above the term "wound" refers to any damage to any tissue of a subject, including damage to the skin as well as damage to deeper tissue. Thereby, the wound may be caused accidentally or be intentionally, or may have been caused by the normal course of a pathological, disease, or degenerative condition. For example, the damage can be as a result of injury or surgery. Non-limiting examples of injuries include ulcers, burns, broken bones, punctures, cuts and scrapes, lacerations, surgical incisions, inflammation, infection, and the like.

The platelet releasates may be administered using the administration methods known to the skilled person, including the use of fluids, aerosols, sprays, mists, lotions, creams, ointments, gels, gums, nebulized droplets or powders, dispensing bottles, pre-soaked fabric, syringes, bandages, dermal patches or plasters, etc. In a preferred embodiment the platelet releasate obtained with the method of this invention can be stored in a stable form in a kit for use in emergency situations for treating wounds. The platelet releasate can be reconstituted for immediate use when needed. In another aspect, the present invention relates to an aerosol, a treatment fluid, a spray, a mist, a lotion, a cream, an ointment, a gel, a gum, a bandage, a dermal patch, a plaster containing the growth factors containing platelete releasate obtained with the method of this invention.

The platelet releasates obtained with the method of this invention may contain increased amounts of growth factors, cytokines, chemokines, etc. Examples of growth factors and other materials that can be present in the releasate include, without limitation, PDGF, PDAF, VEGF, PDEGF, PF-4, TGF-B, FGF-A, FGF-B, TGF-A, IGF-1, IGF-2, BTG, TSP, vWF, PAI-1, IgG, IgM, IgA, KGF, EGF, FGF, TNF, IL-1, KGF-2, fibropeptide A, fibrinogen, albumin, osteonectin, gro-alpha, vitronectin, fibrin D-dimer, favtor V, antithrombin III, a2 macroglobulin, angiogenim, Fg-D, and elastase. In further detail, growth factors, cytokines, or the like that can be present and include, without limitation, LIF, anticancer growth factors such as IGFBP3, eicosanoids such as PGs or leukotrienes, IL-1 TNF alpha, INFs, TNF-a, IL-6, IL-1 (a/b), prostanoid metabolites, complement components, reactive oxygen intermediates, arachidonic acid metabolites, coagulation factors, nitrates, and chemokines. Human derived growth factors, chemokines, cytokines, and hormones can include alpha defensin, alpha synuclein, beta synuclean, 4-1 BBL, 6Ckine, acidic FGF, activin A, avtivin R1b, angiopoietin 2, B-DNF, BAFF, BCA-1, BCA-1, BD-1, BMP-2, BMP-4, BMP-7, BMPRA1, BDNF, CNTF, CTGF, CTI_A-4Fc, CXCL1, CXCL2, cardiotrophin-1, Cripto, Cystatin C, Dkk-1, EGF AOF, EGF, EMAP II, ENA-78, EPO, Eotaxin, FGF basic AOF, FGF-10, FGF-16, FGF 17, FGF 18, FGF19, FGF4, FGF6, FGF7, FGF8, FGF8b, FGF9, Flt3, G-CSF, GDNF, GMCSF, HGF, HGH, IFN alpha A, IFN alpha A/D, IFN alpha D, IFN alpha a2b, IFN, beta 1A, IFN-gamma, IGF1, IGFil, IGFBP-4, IGFBP6, ILI alpha, IL-1Beta, IL10, IL11, IL12, IL13, IL15, IL17, IL17A. IL17F, IL18, IL19, IL2, IL20, IL21, IL23, IL28A, IL28B, IL29, IL3, IL31, IL33, IL4, IL5, IL6, IL7, IL8, IL9, IL10, ITAC, KGF2, Kallikrein1 1, Kallikrein4, Kallikrein7, LEFTY-A, LIF, Leptin, MCSF AOF, MCSF, MCP-1, MCP2, MCP3, MCP4, MDC, MIG, MIP1 alpha, MIP1 beta, MIP3 alpha, MIP3 beta, MIP4, MIP5, midkine, NAP2, NT3, NT4, Neurotactin, neurturin, Oncostatin, osteoprotegrerin, PDGF-AA, PDGF-AB, PDGF-BB, PTN, Rank ligand, Rank receptor, RANTES<SCF, SCFAOF, SDF-1 alpha, SDF-1 Beta, CD4, CD40L, TNF-RI, TNFRII, TARC, TECK, TGF alpha, TGF1 Beta1, TGF Beta2, TGF Beta3, TNF beta/lymphotoxin, TNF-alpha, TPO, TRAIL, TWEAK, and VEGF.

The platelet releasate obtained with the method of the present invention has two main indications in which it proved to be of significant value, although it may be used in other indications as well. The first indication is its use as a therapeutic agent to enhance the proliferation of multi lineage cells in regenerative medicine and in the management of non healing wounds and resistant ulcers. In these applications, the platelet releasate containing growth factors used has been prepared from either human or horse platelets. The platelet releasate obtained with the method of this invention may also be used in cell culture media, in particular stem cells, fibroblasts or dendritic cells. The second indication is as a substitute to fetal bovine serum in in cell culture media. Fibrinogen depleted platelet releasates avoid the undesirable effects of gel formation, and subjecting the releasate to two steps of pathogen/viral reduction ensures product safety. As a result, autologous platelet concentrates are no longer a must, and the mammalian platelet concentrate that is used in the method of this invention may comprises a pool of platelets which originate from different mammalian subjects.

The present invention is further illustrated in the example below.

Example 1

A human was connected to a pheresis machine (Haemonetics_MCS+9000$^a$) so as to obtain a platelet rich concentrate, with platelet count 3-5 times the initial platelet count. The platelet rich concentrate was incubated with Riboflavin and irradiated with UV rays by the MIRASOL™ system as a first step of pathogen reduction. Thereafter, sterile Thrombin$^b$ was added in a suitable concentration of 500 units/cmm to activate the platelets in said concentrate. This gave rise to subsequent release from platelet granules of supra physiological doses of growth factors and cytokines. In addition, activated platelets released the alpha granules content of fibrinogen which is activated by thrombin to form an insoluble clot. When centrifuged, the thrombin treated platelet concentrate separated into a supernatant comprising a clear light red liquid or fluid that consists essentially of lysed platelets, contents of which are supra physiological doses of growth factors released from platelets granules, and a deposit of insoluble fibrin clot. The supernatant was transferred into a new container for further steps of preparation. The platelet releasate was treated with a solvent and detergent system (0.3% TNBP$^c$ and 1% tween 20$^d$), for 1 hour at 31° C. This step is capable of disrupting enveloped viruses (mainly HBC, HCV, and HIV). The solvent and the detergent are there after removed by three consecutive steps of vegetable oil extraction. Sterile castor oil (7.5% of total volume) is added to platelet releasate and mixture is subjected to shaking on a blood mixer for 15 minutes then the container is suspended in an inverted position for 10 minutes to obtain an upper oil phase and a lower platelet lystae phase, which is separated by gravity from the upper phase. This step is repeated for two other times, then the platelet releasate is centrifuged for 20 minutes at 4° C. and 1500 g, in an inverted position to separate any remanants of oil in an upper phase and the platelet releasate in a lower phase that is obtained by gravity Then, the platelet releasate is subjected to a step of Sterile filtering to ensure removal of any bacterial contaminants and then the liquid or fluid filtrate is dispensed in predetermined volumes, (adjusted according to initial platelet counts of concentrate to ensure an equivalent of around 1 million platelets per cm$^3$) in glass vials and lyophilizing such filtrate which consists mainly of platelet derived growth factors.

Example 2

The platelet releasate obtained in example 1 was used to achieve facial rejuvenation. One vial which originated from 2×10$^6$ platelets was injected on each side of the face of a women in the chin, cheek and nasolabial fold. The redness, pain and swelling could be significantly reduced. The regenerative effect lasts for at least 6 months.

Comparative Experiment

A volume which contained 2×10$^6$ autologous platelets was injected on each side of the face of a women, suffering from the same defects as in example 2. The redness, pain and swelling could be reduced to a limited extent only.

Example 3

The platelet releasate obtained in example 1 was used to achieve pain relief in low back pain management. Two vials which originated from 2×10$^6$ platelets were injected in the lower part of the back. The pain could be significantly reduced. The treatment was repeated a week later, by injection of one vial. The regenerative effect lasted for several months.

Example 4

The platelet releasate obtained in example 1 was incorporated into a collagen sodium alginate hydrogel wound dressing, and was applied to a diabetic ulcers that could not be healed for more than 6 months. Within a few days significant wound healing could be achieved.

Example 5

A platelet releasate was prepared according to the method of example 1, this time using horse blood. Two vials which each originated from 2×10$^6$ platelets were injected in injected into an injured muscle of a horse. The treatment was repeated after a week. The muscle healed with no remaining injury.

The invention claimed is:
1. A method for preparing a growth-factors containing platelet releasate from a fluid mammalian platelet concentrate having an initial platelet count, comprising the consecutive steps of
 a. subjecting the platelet concentrate to a first pathogen concentration reduction step with the purpose of disrupting both DNA and RNA of micro-organisms present in the platelet concentrate;
 b. subjecting the platelet concentrate to an activation step by contacting it with an activating agent, with the purpose of causing platelets to release at least part of alpha granules and growth factors present therein, thereby providing a fluid platelet releasate;
 c. subjecting the fluid platelet releasate to a fibrinogen concentration reduction step and recovering a fibrinogen depleted fluid platelet releasate;
 d. subjecting the fibrinogen depleted fluid platelet releasate to a second pathogen concentration reduction step with the purpose of disrupting enveloped viruses;
 e. subjecting the platelet releasate to sterile filtering and recovering from the filtering step a filtrate liquid containing the growth factors;
 f. dividing the filtrate liquid into individual portions which contain the releasate of about 2×10$^5$–2×10$^7$ platelets per cm$^3$, based on the initial platelet count of the platelet concentrate, wherein the volume of the individual portion is adjusted such that each portion contains the releasate of approximately the same number of platelets; and
 g. subjecting the thus obtained individual portions of filtrate liquid to lyophilisation; wherein the growth-factors containing platelet releasate thereby obtained combines characteristics of being lyophilized in reasonable volumes which are suitable for immediate use without requiring further division into suitable aliquots, with ease of storage and reconstitution, and being fibrinogen depleted.

2. The method of claim 1, wherein the activating agent is a solution containing one or more compounds selected from the group of a calcium salt, thrombin, collagen, thromboxane A2 and adenosine diphosphate (ADP).

3. The method according to claim 1, wherein the first pathogen concentration reduction step comprises incubating the platelet concentrate with a photochemical active agent and exposing the platelet concentrate to UV irradiation.

4. The method according to claim 3, wherein the UV irradiation is UVA irradiation.

5. The method according to claim 3, wherein the photochemical active agent is a psoralen.

6. The method of claim 1, wherein the second pathogen concentration reduction step comprises incubating the platelet releasate with a solvent, a detergent, or a combination thereof; followed by removing the solvent, the detergent or the combination thereof; and recovering the platelet releasate depleted for the solvent, the detergent, or the combination thereof.

7. The method of claim 6, wherein the solvent for incubating the platelet releasate is selected from the group consisting of dialkylphosphates and trialkylphosphates.

8. The method of claim 6, wherein the detergent is one or more selected from the group consisting of polyoxyethylene derivatives of fatty acids, partial esters of sorbitol anhydrides, non-ionic detergents, sodium deoxycholate and sulfobetaines.

9. The method according to claim 6, wherein the solvent, the detergent, or the combination thereof is removed from the platelet releasate by oil extraction.

10. The method according to claim 9, wherein the oil extraction is carried out in the presence of an amount of oil which ranges from 2 to 20 weight %, based on the total weight of the mixture of the platelet releasate and the solvent, the detergent, or the combination thereof.

11. The method according to claim 1, further comprising at least one step of centrifugation of the platelet releasate, after removal of the solvent, the detergent, or the combination thereof in the second pathogen concentration reduction step.

12. The method according to claim 1, wherein human albumin is supplied to the filtrate liquid obtained in step e, in advance of subjecting the filtrate liquid to lyophilisation.

13. The method according to claim 1, wherein in advance of subjecting the platelet concentrate to the activation step b, the platelet concentrate is subjected to a leukocyte inactivation step.

14. The method according to claim 1, wherein the mammalian platelet concentrate is rich in growth factors from human platelets or horse platelets.

15. The method according to claim 1, wherein the mammalian platelet concentrate comprises a pool of platelet concentrates which originate from different subjects.

16. The method of claim 2, wherein the activating agent is a thrombin containing solution.

17. The method of claim 4, wherein the UVA irradiation has an energy density between 1 and 10 $J/cm^2$.

18. The method of claim 17, wherein the UVA irradiation has an energy density of 3 $J/cm^2$.

19. The method according to claim 5, wherein the photochemical active agent is amotosalen or riboflavin.

20. The method of claim 7, wherein the solvent for incubating the platelet releasate concentrate is tri-n-butylphosphate.

21. The method of claim 8, wherein the detergent is Triton X-45, Triton X-100 or Tween 80.

22. The method according to claim 10, wherein the oil extraction is carried out in the presence of an amount of oil which ranges from 5 to 15 weight %, based on the total weight of the mixture of the platelet releasate and the solvent and/or detergent.

23. The method according to claim 22, wherein the oil extraction is carried out in the presence of an amount of oil which ranges from 5 to 10 weight %, based on the total weight of the mixture of the platelet releasate and the solvent and/or detergent.

24. The method of claim 1, wherein the filtrate liquid is divided in individual portions which contain the releasate of about $2\times10^6$ platelets per $cm^3$, based on the initial platelet count of the platelet concentrate.

25. A method for at least enhancing proliferation of multilineage cells, promoting wound healing, or ulcer healing; comprising treating a subject in need thereof with an effective amount of the growth-factors containing platelet releasate obtained with the method of claim 1.

26. A cell culture medium for growth of at least stem cells, fibroblasts or dendritic cells; comprising a growth-factors containing platelet releasate obtained with the method of claim 1.

27. A formulation containing the growth-factors containing platelet releasate obtained with the method according to claim 1, which is one or more selected from the group consisting of an aerosol, a treatment fluid, a spray, a mist, a lotion, a cream, an ointment, a gel, a gum, a bandage, a dermal patch, and a plaster.

* * * * *